United States Patent
Main et al.

(10) Patent No.: US 7,594,753 B2
(45) Date of Patent: Sep. 29, 2009

(54) PHANTOM INSERT FOR QUALITY ASSURANCE

(75) Inventors: William T. Main, Aptos, CA (US); Chris B. Charlton, Benicia, CA (US)

(73) Assignee: Accuray Incorporated, Sunnyvale, CA (US)

( * ) Notice: Subject to any disclaimer, the term of this patent is extended or adjusted under 35 U.S.C. 154(b) by 281 days.

(21) Appl. No.: 11/731,043

(22) Filed: Mar. 29, 2007

(65) Prior Publication Data

US 2008/0240364 A1  Oct. 2, 2008

(51) Int. Cl.
*G01D 18/00* (2006.01)
*A61B 6/08* (2006.01)

(52) U.S. Cl. .......... 378/207; 378/205; 250/252.1

(58) Field of Classification Search .......... 378/65, 378/205, 207; 250/252.1, 492.1, 484.4
See application file for complete search history.

(56) References Cited

U.S. PATENT DOCUMENTS

| | | | |
|---|---|---|---|
| 1,252,550 A | 1/1918 | Champney | |
| 5,193,106 A | 3/1993 | DeSena | |
| 6,267,502 B1 | 7/2001 | McNeirney et al. | |
| 6,364,529 B1* | 4/2002 | Dawson | 378/207 |
| 6,501,981 B1 | 12/2002 | Schweikard et al. | |
| 6,516,046 B1 | 2/2003 | Frohlich et al. | |
| 6,528,803 B1 | 3/2003 | Ritt | |
| 6,529,575 B1 | 3/2003 | Hsieh | |
| 6,675,116 B1* | 1/2004 | Ritt | 702/104 |
| 6,842,502 B2 | 1/2005 | Jaffray et al. | |
| 7,056,019 B1* | 6/2006 | Hanson et al. | 378/207 |
| 7,151,253 B2 | 12/2006 | Varchena et al. | |
| 7,187,792 B2 | 3/2007 | Fu et al. | |
| 7,197,830 B2* | 4/2007 | Vaccaro | 33/286 |
| 7,356,120 B2 | 4/2008 | Earnst et al. | |
| 7,402,819 B2* | 7/2008 | Saracen | 250/492.1 |
| 2002/0085668 A1* | 7/2002 | Blumhofer et al. | 378/68 |
| 2003/0220718 A1 | 11/2003 | Jaszczak et al. | |
| 2004/0005035 A1* | 1/2004 | White et al. | 378/207 |
| 2004/0042583 A1* | 3/2004 | Wackerle et al. | 378/65 |
| 2004/0076258 A1 | 4/2004 | Zyromski | |
| 2004/0158146 A1 | 8/2004 | Mate et al. | |
| 2005/0080332 A1 | 4/2005 | Shiu et al. | |

(Continued)

FOREIGN PATENT DOCUMENTS

FR  2854050 A1  10/2004

OTHER PUBLICATIONS

"Dynamic Phantom," CIRS Model 008 Dynamic Thorax Phantom Specifications, pp. 53-54.

(Continued)

*Primary Examiner*—Irakli Kiknadze
(74) *Attorney, Agent, or Firm*—Blakely, Sokoloff, Taylor & Zafman LLP

(57) ABSTRACT

An apparatus for performing quality assurance on a radiation treatment delivery system includes a housing, a target region, and alignment protrusions. The housing is penetrable by a radiation beam of a radiation source of the radiation treatment delivery system and translucent to an image guidance system of the radiation treatment delivery system. The target region is disposed within the housing and contrasts with the housing when imaged by the image guidance system. The alignment protrusions are disposed on the housing for aligning a film insert relative to the target region.

29 Claims, 9 Drawing Sheets

U.S. PATENT DOCUMENTS

| | | | |
|---|---|---|---|
| 2005/0152502 A1* | 7/2005 | Saunders et al. | 378/207 |
| 2005/0234327 A1 | 10/2005 | Saracen et al. | |
| 2006/0239414 A1* | 10/2006 | Foulquier et al. | 378/207 |
| 2007/0071176 A1 | 3/2007 | Main et al. | |
| 2007/0127622 A1 | 6/2007 | Main et al. | |
| 2008/0144776 A1 | 6/2008 | Main et al. | |

OTHER PUBLICATIONS

"Anthropomorphic Phantoms," Radiological Physics Center. Retrieved from http://rpc.mdanderson.org/rpc/services/Anthropomorphic_%20Phantoms/Anth—SRS.htm (Mar. 28, 2007).

"Instructions for SRS Quality Audit System," Radiological Physics Center. Retrieved from http://rpc.mdanderson.org/rpc/services/Anthropomorphic_%20Phantoms/SRSInstrucForInst.pdf (Mar. 28, 2007).

Yu, Cheng Ph.D. et al., "An Anthropomorphic Phantom Study of the Accuracy of CyberKnife Spinal Radiosurgery," Neurosurgery, vol. 55, No. 5, Nov. 2004, pp. 1138-1149.

U.S. Appl. No. 11/234,708, filed Sep. 23, 2005, Main et al., "Integrated Quality Assurance for an Image Guided Radiation Treatment Delivery System".

U.S. Appl. No. 11/273,711, filed Nov. 14, 2005, Main et al., "Unified Quality Assurance for a Radiation Treatment Delivery System".

U.S. Appl. No. 11/293,458, filed Dec. 1, 2005, Michael Saracen, "Respiration Phantom for Quality Assurance".

Low et al. "Minimization of target positioning error in accelerator-based radiosurgery", Medical Physics, Apr. 1995, vol. 22, No. 4, pp. 443-448, especially Abstract, p. 443, col. 2, lines 12-15, p. 443, col. 2, line 22—p. 444, col. 1, line 14, p. 446, section C, Figure 1.

"Rando Phantom" The Phantom Laboratory, New York http://www.phantomlab.com/rando.html.

Data Spectrum Corporation's "Anthropomorphic Torso Phantom" Model ECT/TOR/P as evidenced by U.S. 2003/0220718 A1 ( Jaszczak et al.) Nov. 27, 2003, paragraph 26.

* cited by examiner

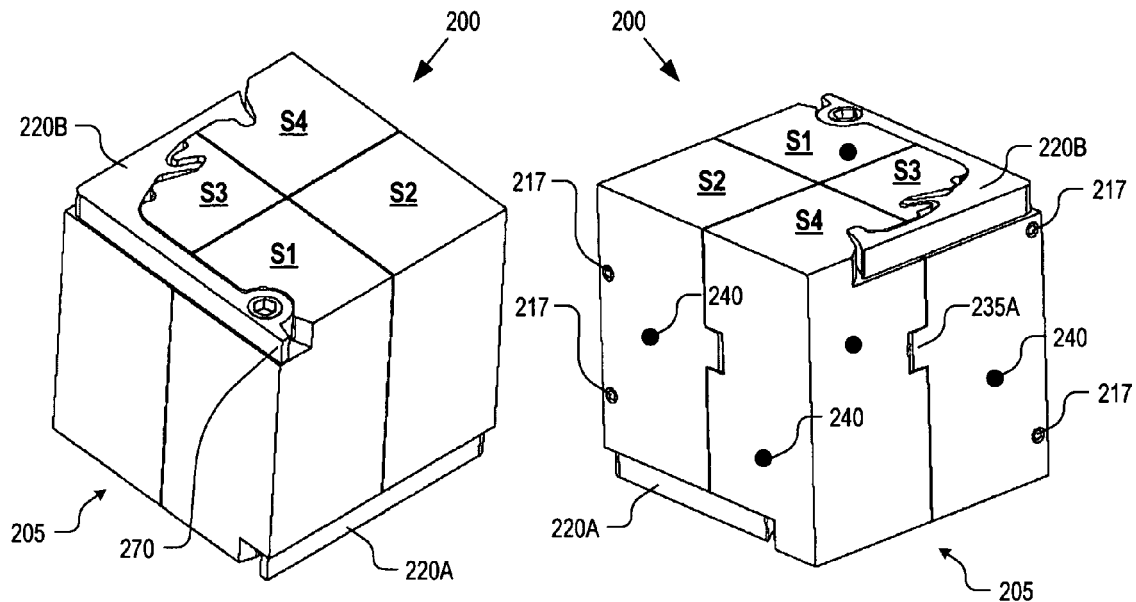
FIG. 2A  FIG. 2B
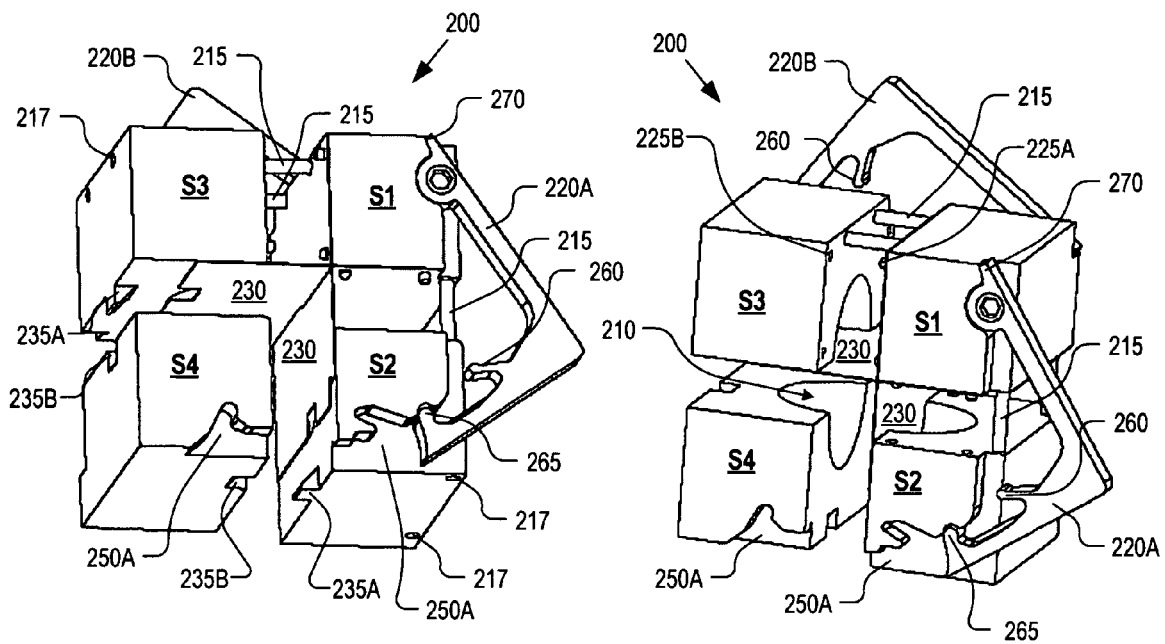
FIG. 2C  FIG. 2D

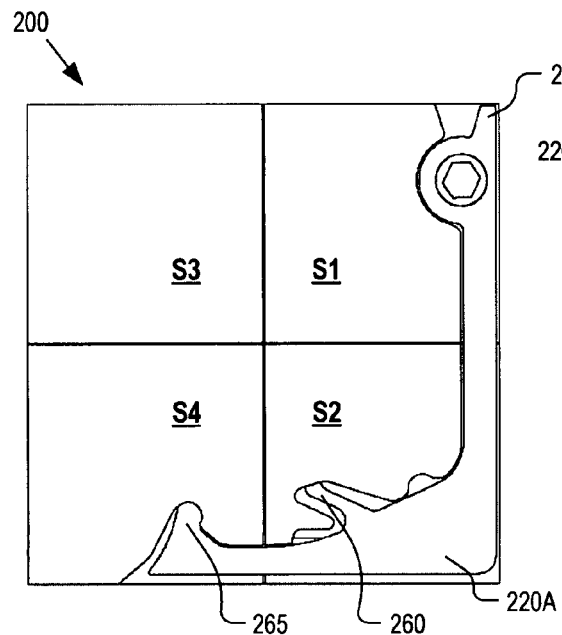
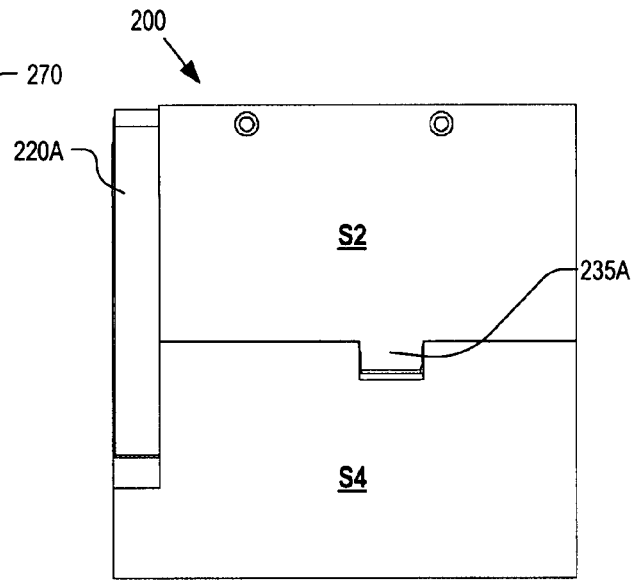
FIG. 3A  FIG. 3B
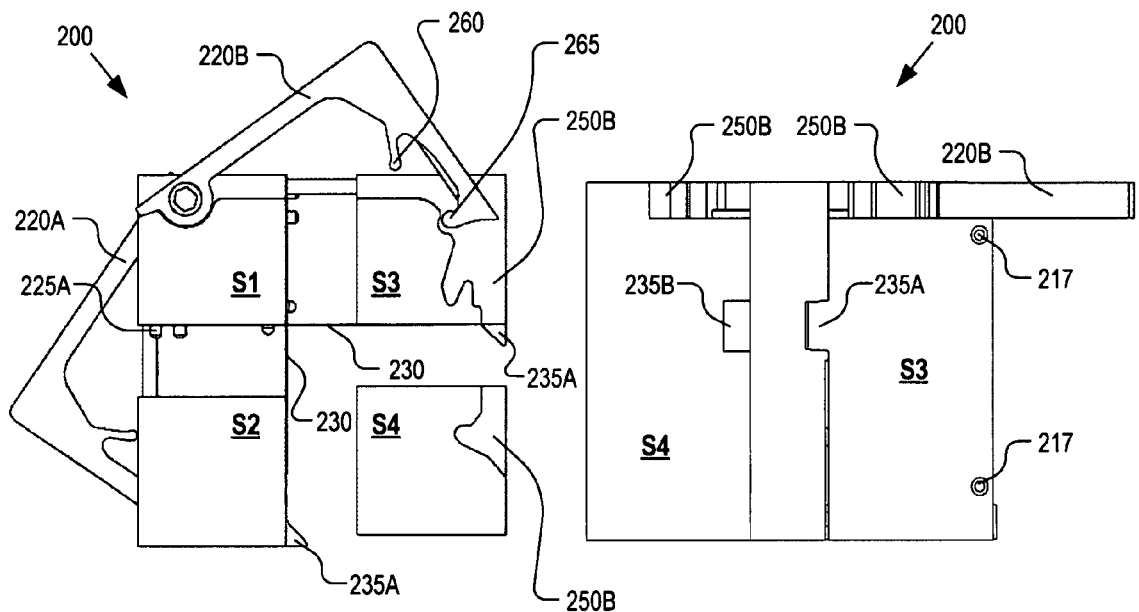
FIG. 3C  FIG. 3D

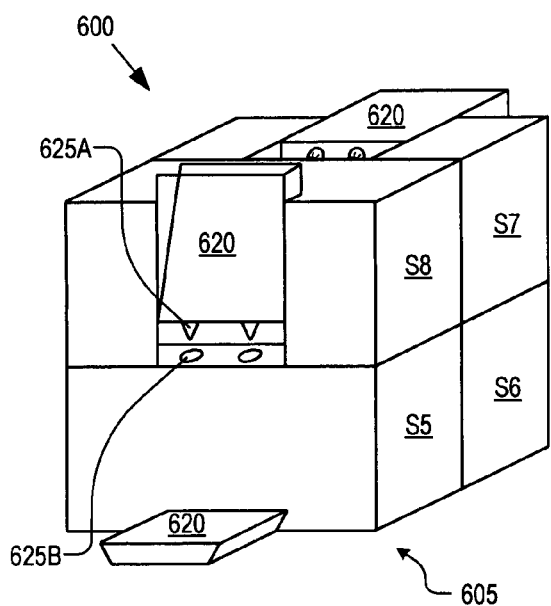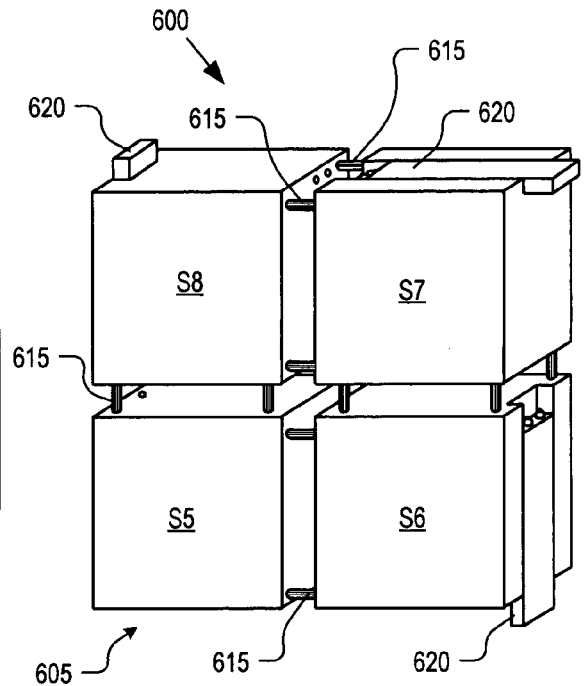
FIG. 6A  FIG. 6B
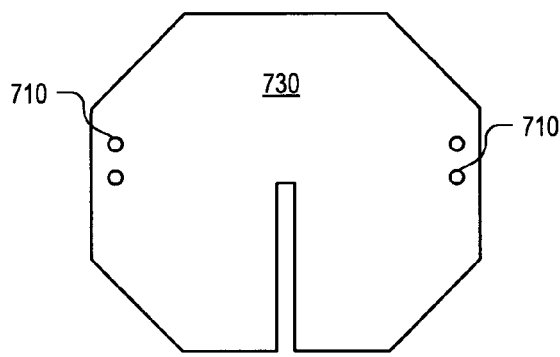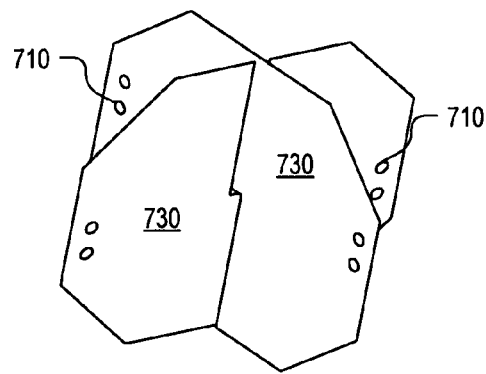
FIG. 7A  FIG. 7B

PHANTOM INSERT FOR QUALITY ASSURANCE

TECHNICAL FIELD

This disclosure relates generally to quality assurance for radiation delivery systems, and in particular but not exclusively, relates to a phantom insert.

BACKGROUND

In radiosurgery or radiotherapy (collectively referred to as radiation treatment) very intense and precisely collimated doses of radiation are delivered to a target region in the body of a patient in order to treat or destroy lesions. Typically, the target region is composed of a volume of tumorous tissue. Radiation treatment requires an extremely accurate spatial localization of the targeted lesions. As a first step in performing radiation treatment, it is necessary to determine with great precision the location of a lesion and any surrounding critical structures, relative to the reference frame of the treatment device. Computed tomography ("CT"), magnetic resonance imaging ("MRI") scans, and other diagnostic imaging modalities enable practitioners to precisely locate a lesion relative to skeletal landmarks or implanted fiducial markers. However, it is also necessary to control the position of the radiation source so that its beam can be precisely directed to the target tissue while avoiding adjacent critical body structures.

Thus, radiation treatment necessitates high precision diagnosis and high precision radiation source control. The consequences of deviating outside the prescribed tolerances for the diagnosis and the radiation source control can be potentially devastating to a patient. Accordingly, quality assurance mechanisms should be implemented to ensure proper alignment and configuration of the radiation delivery system prior to delivering a prescribed radiation dose to a patient.

Conventional quality assurance mechanisms include pointing the radiation source at a quality assurance ("QA") marker, delivering a radiation dose to the QA marker, and then analyzing the QA marker itself to determine if the prescribed dose was actually delivered to the correct location. If the prescribed dose was delivered as expected, then the radiation treatment delivery system is deemed properly aligned. If the prescribed dose was not delivered as expected, then the radiation treatment delivery system is deemed misaligned.

Conventional QA markers include silver loaded gel capsules or photographic film inserts that can store readable information about the distribution of the radiation dose delivered to the QA marker. However, extracting this alignment information from silver loaded gels is a time consuming and costly task. Similarly, photographic film inserts are not easily inserted into or extracted from conventional QA markers, nor are the photographic film inserts easily aligned with the housing of the QA marker. As such, these conventional QA markers are time consuming and prone to human error.

BRIEF DESCRIPTION OF THE DRAWINGS

Non-limiting and non-exhaustive embodiments of the invention are described with reference to the following figures, wherein like reference numerals refer to like parts throughout the various views unless otherwise specified.

FIG. 2A is a perspective view illustrating a quality assurance marker in a closed position, in accordance with an embodiment of the invention.

FIG. 2B is another perspective view illustrating a quality assurance marker in a closed position, in accordance with an embodiment of the invention.

FIG. 2C is a perspective view illustrating a quality assurance marker in an open position, in accordance with an embodiment of the invention.

FIG. 2D is another perspective view illustrating a quality assurance marker in an open position, in accordance with an embodiment of the invention.

FIG. 3A is a side view illustrating a quality assurance marker in a closed position, in accordance with an embodiment of the invention.

FIG. 3B is another side view illustrating a quality assurance marker in a closed position, in accordance with an embodiment of the invention.

FIG. 3C is a side view illustrating a quality assurance marker in an open position, in accordance with an embodiment of the invention.

FIG. 3D is another side view illustrating a quality assurance marker in an open position, in accordance with an embodiment of the invention.

FIG. 6A is a perspective view illustrating another quality assurance marker in a closed but unlocked position, in accordance with an embodiment of the invention.

FIG. 6B is a perspective view illustrating the other quality assurance marker in an open position, in accordance with an embodiment of the invention.

FIG. 7A is a plan view illustrating a film insert for inserting into a quality assurance marker, in accordance with an embodiment of the invention.

FIG. 7B is a perspective view illustrating two interlocked film inserts for inserting into a quality assurance marker, in accordance with an embodiment of the invention.

DETAILED DESCRIPTION

Embodiments of an apparatus, system, and method for quality assurance of a radiation treatment delivery system are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Figure 1:
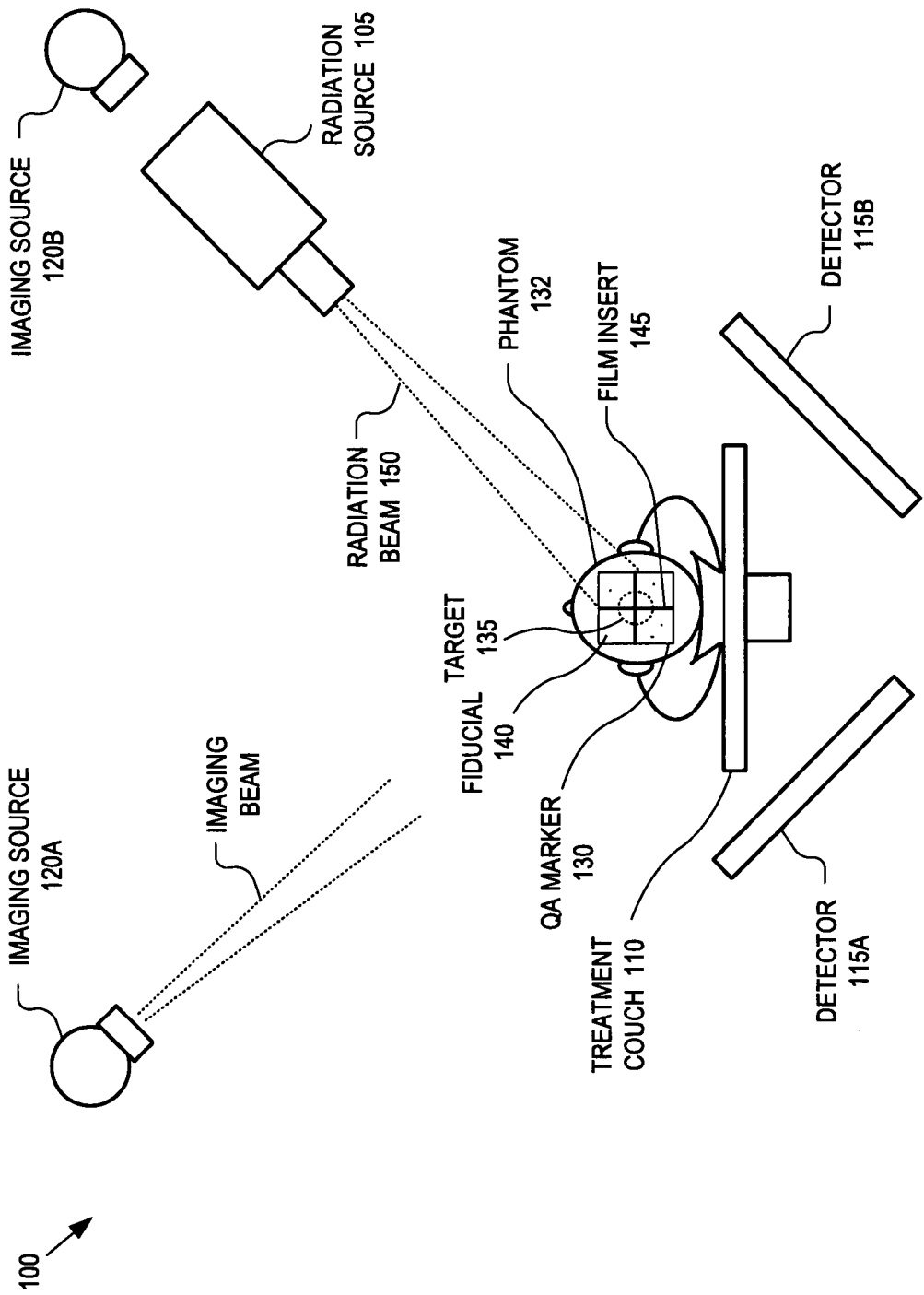
FIG. 1 is a diagram illustrating use of a quality assurance marker to execute a confidence check on an image guided radiation treatment delivery system, in accordance with an embodiment of the invention.

FIG. 1 is a diagram illustrating use of a quality assurance ("QA") marker to execute a confidence check on an image guided radiation treatment delivery system 100, in accordance with an embodiment of the invention. The illustrated embodiment of radiation treatment delivery system 100 includes a radiation source 105, a treatment couch 110, detectors 115A and 115B (collectively 115, also referred to as imagers), and imaging sources 120A and 120B (collectively 120).

Radiation treatment delivery system 100 may be used to perform radiosurgery to treat or destroy lesions within a patient. During radiosurgery, the patient rests on treatment couch 110 and the treatment couch is maneuvered to position the lesion or volume of interest ("VOI") to a preset position or within an operating range accessible to radiation source 105 (e.g., field of view). In one embodiment, radiation treatment delivery system 100 is an image guided radiation treatment delivery system. Together, imaging sources 120 and detectors 115 are an image guidance system that provides visual control over the position of treatment couch 110 and the patient thereon. In one embodiment, treatment couch 110 may be coupled to a positioning system (e.g., robotic arm) that receives feedback from the image guidance system to provide accurate control over both the displacement and orientation of the VOI within the patient and radiation source 105.

Periodically, it is important to execute quality assurance ("QA") mechanisms to ensure radiation treatment delivery system 100 is properly aligned and configured as specified to accurately deliver a prescribed dose of radiation to a patient. These QA mechanisms, also referred to as confidence checks or end-to-end tests, validate that the imaging system, the positioning system (not illustrated), treatment couch 110, and radiation source 105 are all calibrated and aligned with each other.

A QA marker 130 may be used to perform one of these confidence checks. In one embodiment, QA marker 130 may be inserted into an anthropomorphic phantom 132, which is then placed on treatment couch 110. Because QA marker 130 is inserted into anthropomorphic phantom 132 it is commonly referred to as a "phantom insert." The illustrated embodiment of anthropomorphic phantom 132 is shaped to resemble the head, neck, and upper shoulders of a patient to simulate treatment plans to be executed on these portions of the human body. For example, anthropomorphic phantom 132 may include cavities within the head or neck areas into which QA marker 130 may be inserted. Treatment plans may then be generated for the anthropomorphic phantom 132 with the QA marker 130 placed therein to simulate the tumorous tissue or VOI, the treatment plan delivered to the QA marker 130 through the anthropomorphic phantom 132, and the QA marker 130 analyzed to determine if the prescribed treatment plan was accurately delivered. Although anthropomorphic phantom 132 is shaped as a head, neck, and upper shoulder region of a patient, it should be appreciated that other anthropomorphic phantoms may resemble other anatomical regions including a chest, a torso, an abdomen, a leg, an arm, or otherwise.

The illustrated embodiment of QA marker 130 includes a target 135, fiducials 140, and film inserts 145 passing through target 135. Fiducials 140 are embedded within QA marker 132 and used by the image guidance system to position QA marker 130 to a preset position. In one embodiment, image guidance system emits x-rays and fiducials 140 are made of gold or other dense metals. Subsequently, radiation source 105 is maneuvered to one or more positions to take aim at target 135. From each position, radiation source 105 emits a radiation beam 150 along a trajectory passing through QA marker 130 and impinging upon film inserts 145 to deliver prescribed doses of radiation per the treatment plan.

In response to radiation beams 150, film inserts 145 are exposed and an exposure image or delivered dose image is developed on each film insert 145. QA marker 130 may then be pulled from anthropomorphic phantom 132 and film inserts 145 removed from QA marker 130 for analyzing. By analyzing the shape, size, position, and/or optical density (i.e., amount of exposure represented by shade) of the exposure images on each film insert 145, alignment and/or calibration of radiation source 105 can be validated or a misalignment/invalid calibration exposed.

By emitting multiple radiation beams from different positions, multi-dimensional alignment validation can be achieved. In one embodiment, QA marker 130 provides three-dimensional translational alignment validation. In one embodiment, QA marker 130 provides both three-dimensional translational alignment validation and rotational (e.g., roll, pitch, yaw) alignment validation. Translational/rotational alignment validation includes validating the ability of the image guidance system and the positioning system to achieve accurate translational/rotational placement of QA marker 130 at the preset position and the ability of radiation source 105 to arrive at its translational/rotational preset position.

The embodiment of FIG. 1 illustrates two film inserts 145 that slice through the center of target 135 in two perpendicular planes. However, it should be appreciated that one or many film inserts 145 may be used and that the planes along which film inserts 145 reside may assume other orientations. Since film inserts 145 merely slice through two-dimensional planes within QA marker 130, the delivered dose image developed thereon will only capture two dimensional slices of the actual dose delivered. Accordingly, treatment planning software may be used to determine calculated doses that should be delivered along these planes, if the prescribed dose is accurately delivered. In one embodiment, the treatment planning software generates calculated iso-dose lines (similar to a topographical survey) along the two-dimensional planes based on the three-dimensional conformal dose calculated by the treatment plan. In turn, film inserts 145 may be extracted after delivery of the treatment plan and the exposure image scanned. The scanned delivered dose image may then be converted into iso-dose lines, which are subsequently compared to the calculated iso-dose lines to determine whether the delivered dose matches the calculated dose.

Film inserts 145 may include standard (MD) radiochromic film, high-sensitivity ("HS") radiochromic film, or the like. Of course, the type of film used may affect the exposure density to dose relationship. Accordingly, in one embodiment, prior to executing the confidence checks discussed herein, a film insert 145 from a batch of film inserts 145 may first be exposed to one or more known doses of radiation to generate an optical density step tablet to function as a calibration reference. Subsequently, the dose delivered to each film insert 145 may be determined by analyzing and comparing the exposure density (e.g., shades of grey) within the delivered dose images against the optical density step tablet.

FIGS. 2A-2D and 3A-3D illustrate a QA marker 200, in accordance with an embodiment of the invention. QA marker 200 is one possible embodiment of QA marker 130 illustrated in FIG. 1. FIGS. 2A and 2B are perspective views illustrating QA marker 200 in a closed position, while FIGS. 2C and 2D are perspective views illustrating QA marker 200 in an open position. FIGS. 3A and 3B are side views illustrating QA marker 200 in a closed position, while FIGS. 3C and 3D are side views illustrating QA marker 200 in an open position. It should be appreciated that the size, shapes, and orientations of the various components of QA marker 200 may not be illustrated to scale.

The illustrated embodiment of QA marker 200 includes a housing 205, a target region 210, connectors 215, locking mechanisms 220A and 220B, film alignment structures 225A and 225B, film inserts 230, housing alignment structures 235A and 235B, and embedded fiducials 240 (only illustrated in FIG. 2B so as not to clutter the drawings). The illustrated embodiment of housing 205 includes four quadrants or sections S1, S2, S3, and S4. The illustrated embodiment of sections S2 and S3 include holes 217 into which connectors 215 may slide and sections S2, S3, and S4 include grooves 250A and 250B for engaging locking mechanisms 220A and 220B, respectively. The illustrated embodiment of locking mechanism 220A and 220B include flexible splines 260 and hooks 265. It should be appreciated that only a portion of some features are labeled in FIGS. 2A-D and 3A-D so as not to clutter the drawings.

Housing 205 may be formed of a variety of materials that are transparent, or at least translucent, to the imaging beams (e.g., x-rays) of imaging source 120 and penetrable by radiation source 105. In one embodiment, housing 205 including sections S1, S2, S3, and S4 are fabricated of ABS (Acrylonitrile Butadiene Styrene) thermoplastic. The illustrated embodiment of housing 205 is a cube having a size convenient for inserting into anatomical phantoms (e.g., 2.5 inches for inserting into a head phantom or 1.25 inches for inserting into a neck phantom). However, it should be appreciated that housing 205 may assume other shapes, materials, or dimensions convenient for inserting into anthropomorphic phantom 132 or for standing alone on treatment couch 110.

Housing 205 may be impregnated with tracking fiducials 240 fabricated of a high density metal (e.g., gold) for easy identification and tracking by the image guidance system. Fiducials 240 may be regularly distributed or randomly distributed throughout housing 205. The image guidance system uses images of fiducials 240 gathered in real-time to register against a reference image of QA marker 200 gathered during diagnostic imaging.

The illustrated embodiment of target region 210 is a spherical void for holding a spherical target 135. Because the illustrated embodiment of QA marker 200 has a cube shaped housing 205 and a spherical target 135, it is often referred to as a ball-cube insert.

Figure 5:
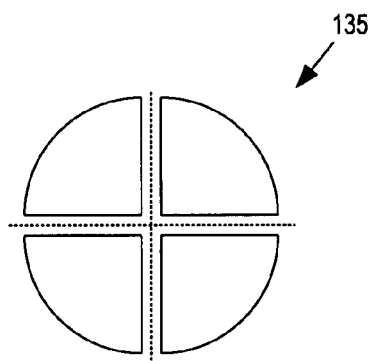
FIG. 5 is a plan view illustrating a separable target for inserting into a quality assurance marker, in accordance with an embodiment of the invention.

FIG. 5 illustrates one embodiment of target 135. As illustrated, target 135 is separable to allow film inserts 145 to pass through. The individual parts of target 135 may be removable from housing 205 to allow targets of different materials to be swapped out or the individual pieces permanently fixed into target region 210. Target 135 is fabricated of one or more materials that provide imaging contrast to housing 205 (e.g., acrylic) to enable the image guidance system to visually identify and track target 135. In fact, target 135 is intended to represent a VOI (e.g., tumorous lesion within a patient) at which radiation treatment delivery system 100 is directed to treat with radiation. Target region 210 and therefore target 135 may assume various symmetrical shapes (e.g., oval) or nonsymmetrical shapes to represent irregularly shaped VOIs. In an embodiment where housing 205 is approximately 2.5 inches square, target region 210 may be approximately 1.25 inches in diameter.

Locking mechanism 220A and 220B (collectively 220) are provided to secure QA marker 200 in the closed position and to prevent sections S2 and S3 from separating from section S1 when QA marker 200 is the open position. The illustrated embodiment of locking mechanism 220 includes two latches or clips pivotally mounted to either side of section S1 of housing 205. The latches may be fabricated of Delrin, Nylon, other polymer materials having a similar density to ABS plastic used to fabricate sections S1, S2, S3, and S4, or otherwise.

While in the closed position, hooks 265 on each latch lock onto corresponding notches in grooves 250A and 250B within section S4 to hold section S4 in place. Locking mechanisms 220 further include flexible splines 260 located on each latch that also mate with corresponding notches in grooves 250A and 250B. Flexible splines 260 exert an urging force that urges section S2 and S3 towards section S1 when locking mechanism 220 is engaged and housing 205 closed.

Housing 205 may be opened to gain access to removable film inserts 230. To open housing 205, locking mechanisms 220 are unclasped by applying a force to hooks 265 and rotating the latches counterclockwise. Once the latches are pivoted to the open position, sections S2 and S3 can slide apart from section S1 on connectors 215. In one embodiment, connectors 215 are rigidly fixed to section S1 but slide along guide holes 217 within sections S3 and S2. Connectors 217 constrain sections S2 and S3 to slide along an axis perpendicular to inside surfaces of section S1. A stopper 270 is disposed near the pivot mount of each latch and butts up against a cutout groove in housing section S1 to constrain the opening angle of the latches. Stoppers 270 prevent the latches from hyper-extending to ensure that hooks 265 will engage a notch in groove 250A on section S2 (see FIG. 2C) and a notch in groove 250B on section S3 (see FIG. 3C) when housing 205 is in the open position. These notches mate with hooks 265 to prevent sections S2 and S3 from sliding off a distal end of connectors 215. In the illustrated embodiment, only section S4 is allowed to completely separate from the other sections S1, S2, and S4 to gain access to film inserts 230. In one embodiment, connectors 215 are fabricated of PEEK (PolyEtherEther-Ketone) thermoplastic.

When housing 205 is closed, section S4 is passively aligned to sections S2 and S3 via housing alignment structures 235A and 235B (collectively 235). Housing alignment structures 235A are disposed on sections S3 and S2 and mate with corresponding housing alignment structures 235B disposed on section S4. The illustrated embodiment of housing alignment structures 235A are shaped like protruding ramps that guide removable section S4 into alignment when housing 205 is closed. In one embodiment, alignment structures 235 are off centered along the side of sections S2, S3, and S4 to prevent section S4 from being symmetrical so that it can only be fitted to sections S2 and S3 one way.

Film alignment structures 225A and 225B (collectively 225) are disposed on inside surfaces of sections S1, S2, and S3 to passively align film inserts 230. In the illustrated embodiment, film alignment structures 225A are protrusions that mate with film alignment structures 225B, which in the illustrated embodiment are corresponding recesses. In one embodiment, film alignment structures 225A are PEEK thermoplastic protrusions with metal (e.g., copper) fiducials embedded therein. When film inserts 230 are mounted into housing 205, film alignment structures 225A insert through corresponding cutouts in film inserts 230. In this manner film alignment structures 225A ensure that film inserts 230 are always aligned relative to target region 210.

Figure 4:
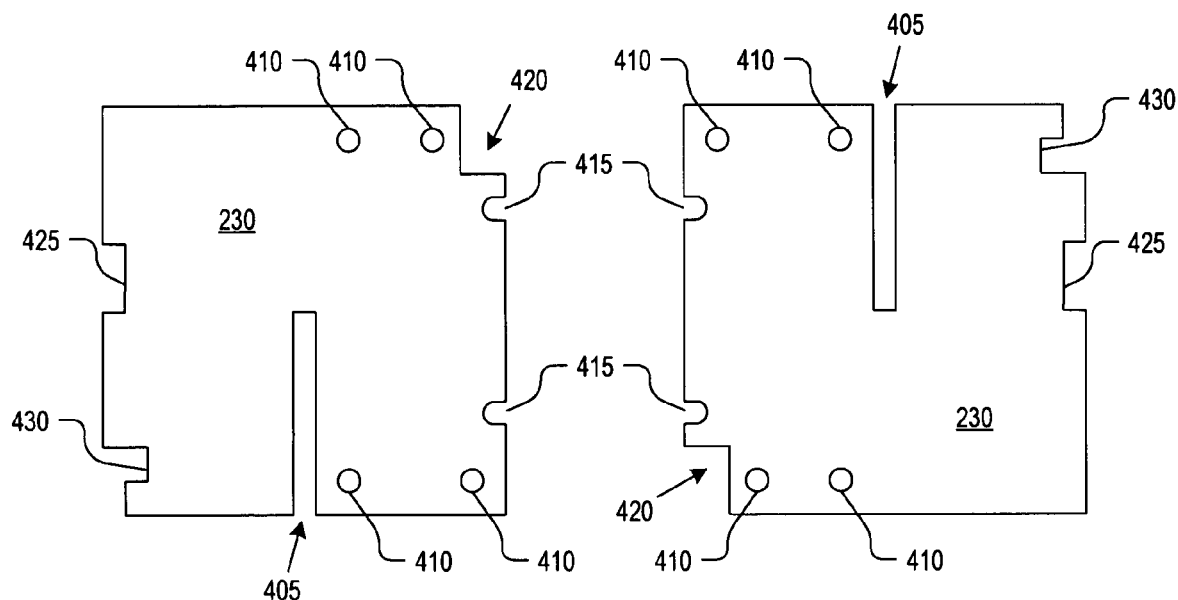
FIG. 4 is a plan view illustrating two film inserts for inserting into a quality assurance marker, in accordance with an embodiment of the invention.

FIG. 4 illustrates film inserts 230, in accordance with an embodiment of the invention. Film inserts 230 corresponding to one possible implementation of film inserts 145 illustrated in FIG. 1. In one embodiment, film inserts 230 are laser cut to precisely fit into QA marker 200. The illustrated embodiment of film inserts 230 include slits 405, interior cutouts 410, and exterior cutouts 415, 420, 425, and 430.

Prior to mounting film inserts 230 into housing 205, the two film inserts 230 are slid together by positioning film inserts 230 perpendicular to each other and mating slits 405. Subsequently, the two film inserts 230 are mounted into housing 205 while ensuring that interior cutouts 410 and exterior cutouts 415, 420, 425, and 430 mate with their corresponding features on QA marker 200. In particular, film alignment structures 225A pass through interior cutouts 410, exterior cutouts 415 fit around connectors 215, exterior cutouts 425 fit around housing alignment structures 235A, and exterior cutouts 420 and 430 provide clearance for locking mechanisms 220A and 220B. In one embodiment, due to the nonsymmetrical nature of the interior and exterior cutouts, film inserts 230 can only be inserted into housing 205 in a single orientation.

FIGS. 6A and 6B illustrate a QA marker 600, in accordance with an embodiment of the invention. FIG. 6A illustrates QA marker 600 in a closed, but unlocked position and FIG. 6B illustrates QA marker 600 in an open position. QA marker 600 is another possible implementation of QA marker 130 illustrated in FIG. 1. The illustrated embodiment of QA marker 600 includes a housing 605, a target region (not illustrated) for housing a target (e.g., target 135), connectors 615, locking mechanisms 620, and film alignment structures 625A and 625B. The illustrated embodiment of housing 605 includes four sections S5, S6, S7, and S8.

QA marker 600 is provided to house removable film inserts 730 (illustrated in FIGS. 7A and 7B) and is similar to QA marker 200 with the following highlighted exceptions. Sections S5, S6, S7, and S8 separate by sliding along connectors 615 to allow insertion of film inserts 730. However, sections S5, S6, S7, and S8 are locked in the closed position by locking mechanisms 620, which resemble sliders that slide within dovetail grooves formed in respective sections S5, S6, S7, and S8. When the sliders are slid into the lock position, film alignment structures 625A pass through interior cutouts 710 within film inserts 730 and mate with corresponding film alignment structures 625B.

Because all four sections S5, S6, S7, and S8 slide together at the same time, when closing housing 605, alignment structures 625A trace out a non-perpendicular path relative to the path traced out by their corresponding alignment structures 625B. Accordingly, in the illustrated embodiment, alignment structures 625A are optionally cone or pyramid shaped to prevent binding during the closing action.

Figure 8:
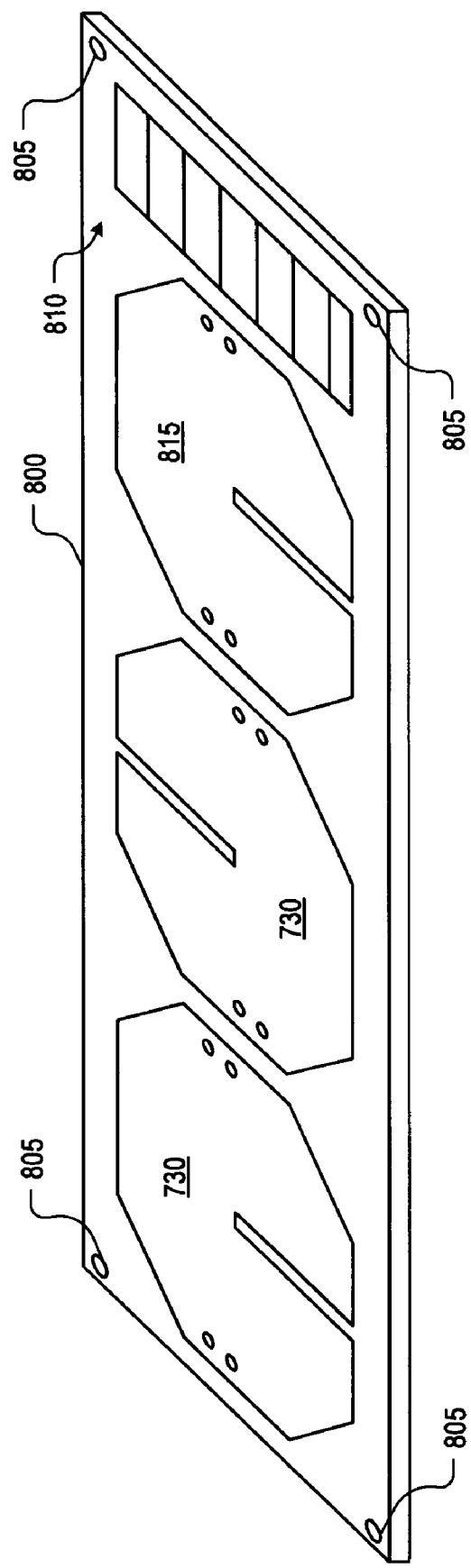
FIG. 8 is a perspective view illustrating a scanning base for supporting film inserts during an optical scanning process, in accordance with an embodiment of the invention.

FIG. 8 is a perspective view illustrating a scanning base 800 for supporting film inserts during an optical scanning process, in accordance with an embodiment of the invention. FIG. 8 illustrates film inserts 730 placed on scanning base 800; however, it should be appreciated that scanning base 800 is equally applicable for use with film inserts 230.

The illustrated embodiment of scanning base 800 includes registration markers 805, an optical density step tablet 810, a background film 815, and film inserts 730 disposed thereon. Film inserts 730 (or film inserts 230) are placed on scanning base 800 after delivering a treatment plan of radiation thereto. Scanning base 800 provides a rigid base for scanning the delivered dose images into a computer. Registration markers 805 (e.g., metal hemispheres) are precisely positioned to allow for optical scanner calibration and registration. Optical density step tablet 810 may be used for grey scale calibration, while background film 815 is an unexposed film insert provided for grey scale reference of unexposed film.

Figure 9:
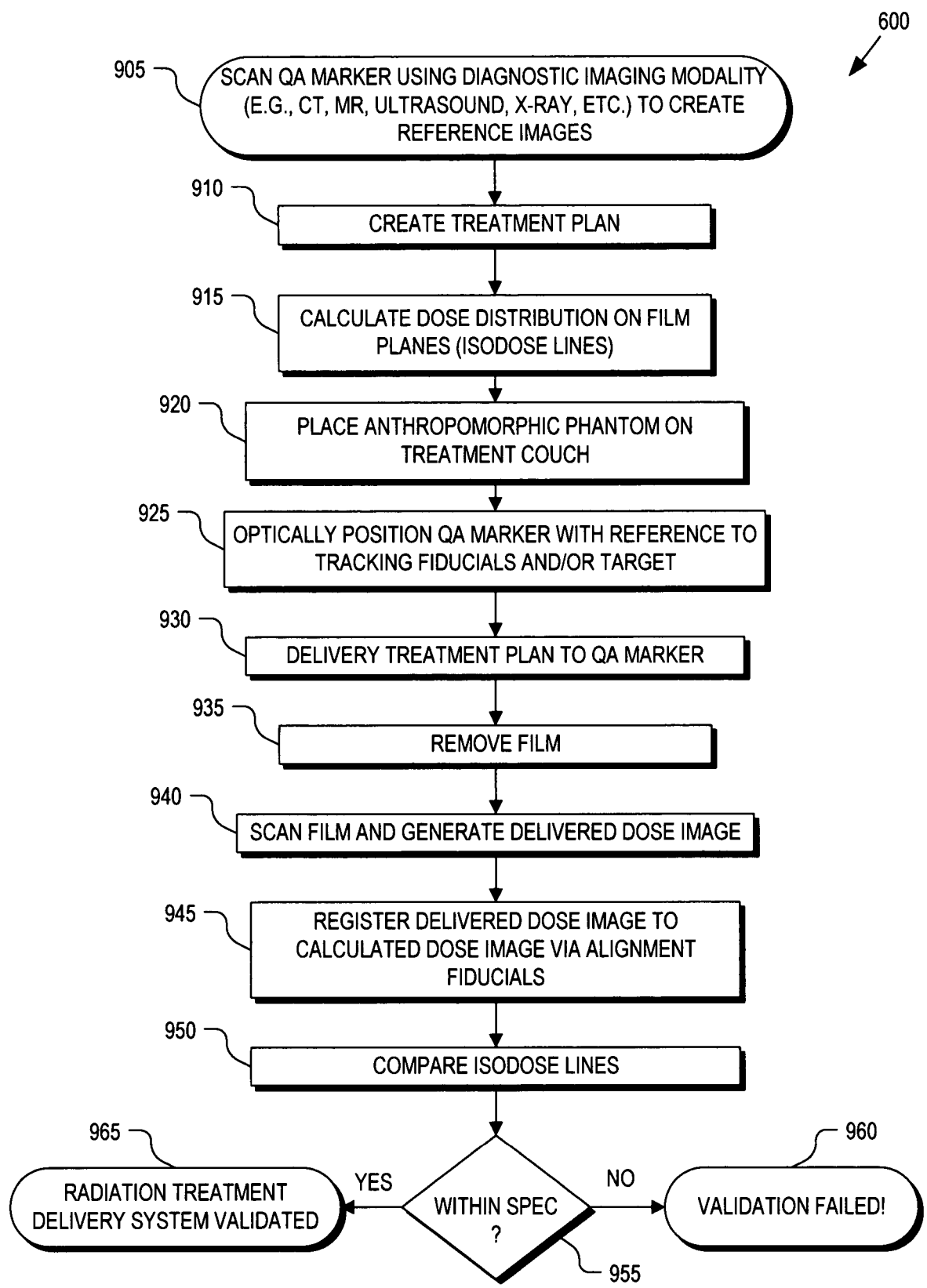
FIG. 9 is a flow chart illustrating a process for performing a quality assurance confidence check on a radiation treatment delivery system, in accordance with an embodiment of the invention.

FIG. 9 is a flow chart illustrating a process 900 for performing a QA confidence check on a radiation treatment delivery system 100 using QA marker 130, in accordance with an embodiment of the invention. The order in which some or all of the process blocks appear in process 900 should not be deemed limiting. Rather, one of ordinary skill in the art having the benefit of the present disclosure will understand that some of the process blocks may be executed in a variety of orders not illustrated, or even in parallel.

In a process block 905, QA marker 130 is placed inside anthropomorphic phantom 132 and scanned using a diagnostic imaging modality, such as, computed tomography ("CT") system, a magnetic resonance imaging ("MRI") system, a positron emission tomography ("PET") system, an ultrasound system, or the like. The diagnostic scan of QA marker 130 and anthropomorphic phantom 132 is executed to generate reference images for calculating a proposed treatment plan, which is subsequently generated in process block 910. The anatomical shape of anthropomorphic phantom 132 may be selected based upon the anatomy the QA test is attempting to simulate.

In a process block 915, the 3-dimensional treatment plan is analyzed to determine calculated dose distributions that will fall along planes slicing through target 135 that are coincident with film inserts 145. In one embodiment, these calculated dose distributions include calculated iso-dose lines co-incident with the planes of film inserts 145.

After the treatment plan has been calculated, anthropomorphic phantom 132 with QA marker 130 inserted therein is placed upon treatment couch 110 (process block 920) and positioned to a selected location within the operating envelop of radiation source 105 under visual control of the image guidance system. The image guidance system may use both tracking fiducials 140 and optical recognition of target 135 itself to correctly position QA marker 130 relative to radiation source 105 (process block 925).

In a process block 930, the calculated treatment plan is delivered to target 135 by radiation treatment delivery system 100. Delivery of the calculated treatment plan may include radiation source 105 delivering many individual doses from different trajectories. For one end-to-end test, the calculated treatment plan may simply attempt to delivery a treatment dose to a spherical VOI that is coincident with target 135. For a conformal test, the calculated treatment plan may attempt to deliver a treatment dose to an arbitrarily shaped VOI (e.g., hemisphere) to test the ability of radiation treatment delivery system 100 to delivery radiation to irregularly shaped VOIs with a high degree of conformality (the degree to which the radiation dose matches or conforms to the shape and extent of the target VOI in order to avoid damage to critical adjacent structures) and homogeneity (uniformity of the radiation dose over the VOI).

After the treatment plan is delivered, film inserts 145 are extracted from QA marker 130 (process block 935) and scanned into a computer (process block 940) to generate a delivered dose image. In one embodiment, the delivered iso-dose lines are calculated based on the delivered dose image scanned into the treatment planning software.

In a process block 945, the delivered dose images are registered to the calculated dose images to ensure proper image alignment when comparing the two sets of iso-dose lines. In one embodiment, the calculated dose image and the delivered dose image are registered by concentrically aligning the images of the metal fiducials (e.g., copper fiducials) embedded within film alignment structures 225A (or 625A) obtained from the diagnostic scan executed in process block 905 with the images of the interior cutouts 410 obtained from scanning the delivered dose images.

In a process block 950, the delivered dose images are compared against the calculated dose images to determine whether the delivered dose was delivered to the VOI within tolerances prescribed by the treatment plan. In one embodiment, the delivered dose images and the calculated dose images are compared by measuring the degree of deviations between iso-dose lines in the two images.

If the deviations are not within specified tolerances (decision block 955), then radiation treatment delivery system 100 is deemed misaligned or incorrectly calibrated and the confidence check is failed (process block 960). If the deviations are within specified tolerances (decision block 955), then radiation treatment delivery system 100 is deemed aligned and correctly calibrated, and the confidence check is passed (process block 965).

Figure 10:
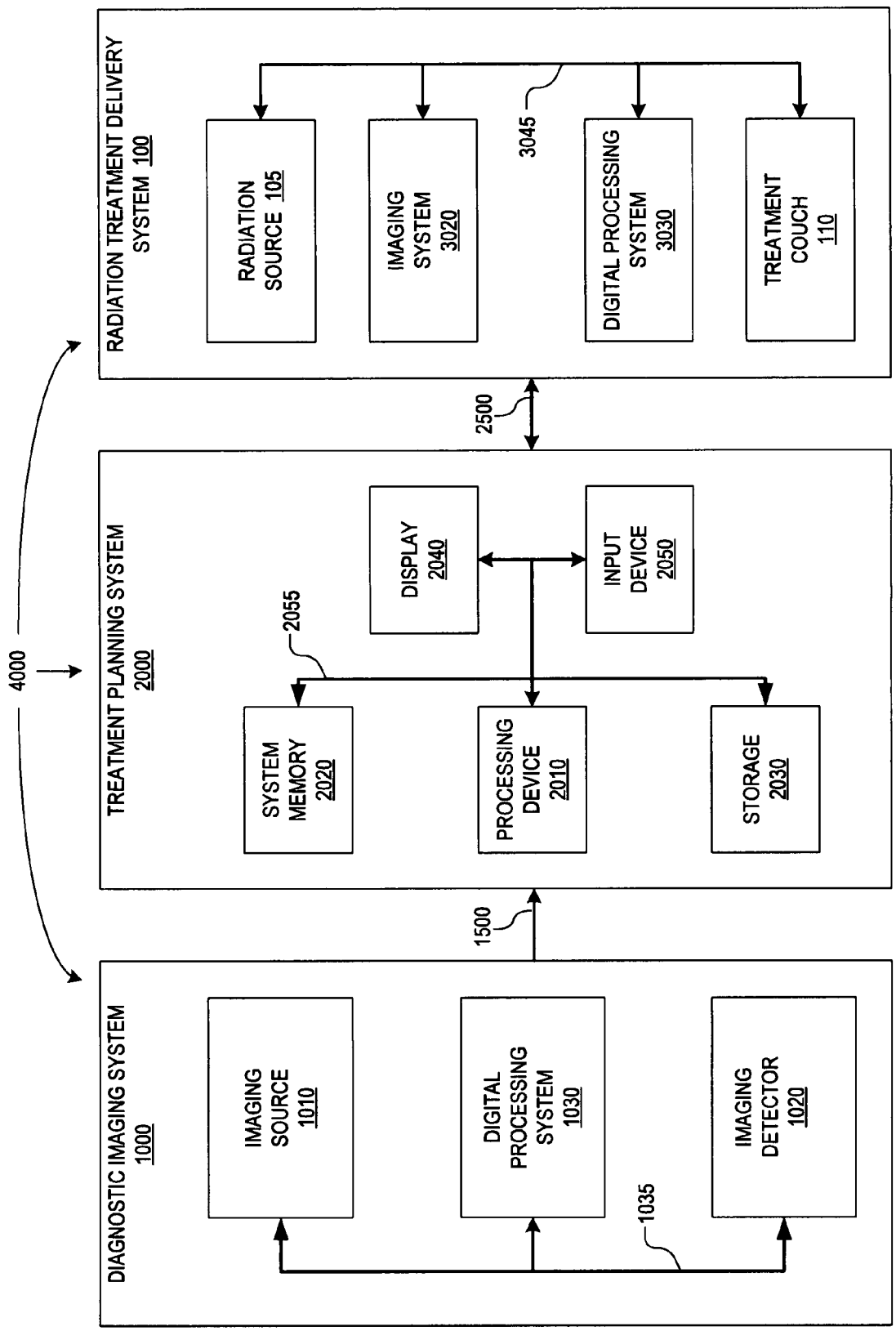
FIG. 10 is a block diagram illustrating a therapeutic patient treatment system for generating diagnostic images, generating a treatment plan, and delivering the treatment plan, in accordance with an embodiment of the invention.

FIG. 10 is a block diagram illustrating a therapeutic patient treatment system 4000 for generating diagnostic images, generating a treatment plan, and delivering the treatment plan to a patient, in which features of the present invention may be implemented. As described below and illustrated in FIG. 10, systems 4000 may include a diagnostic imaging system 1000, a treatment planning system 2000 and a radiation delivery system 100.

Diagnostic imaging system 1000 may be any system capable of producing medical diagnostic images of the VOI within a patient that may be used for subsequent medical diagnosis, treatment planning and/or treatment delivery. For example, diagnostic imaging system 1000 may be a computed tomography ("CT") system, a magnetic resonance imaging ("MRI") system, a positron emission tomography ("PET") system, an ultrasound system or the like. For ease of discussion, diagnostic imaging system 1000 may be discussed below at times in relation to a CT x-ray imaging modality. However, other imaging modalities such as those above may also be used.

Diagnostic imaging system 1000 includes an imaging source 1010 to generate an imaging beam (e.g., x-rays, ultrasonic waves, radio frequency waves, etc.) and an imaging detector 1020 to detect and receive the beam generated by imaging source 1010, or a secondary beam or emission stimulated by the beam from the imaging source (e.g., in an MRI or PET scan). In one embodiment, diagnostic imaging system 1000 may include two or more diagnostic X-ray sources and two or more corresponding imaging detectors. For example, two x-ray sources may be disposed around a patient to be imaged, fixed at an angular separation from each other (e.g., 90 degrees, 45 degrees, etc.) and aimed through the patient toward (an) imaging detector(s) which may be diametrically opposed to the x-ray sources. A single large imaging detector, or multiple imaging detectors, can also be used that would be illuminated by each x-ray imaging source. Alternatively, other numbers and configurations of imaging sources and imaging detectors may be used.

The imaging source 1010 and the imaging detector 1020 are coupled to a digital processing system 1030 to control the imaging operation and process image data. Diagnostic imaging system 1000 includes a bus or other means 1035 for transferring data and commands among digital processing system 1030, imaging source 1010 and imaging detector 1020. Digital processing system 1030 may include one or more general-purpose processors (e.g., a microprocessor), special purpose processor such as a digital signal processor ("DSP") or other type of device such as a controller or field programmable gate array ("FPGA"). Digital processing system 1030 may also include other components (not shown) such as memory, storage devices, network adapters and the like. Digital processing system 1030 may be configured to generate digital diagnostic images in a standard format, such as the DICOM (Digital Imaging and Communications in Medicine) format, for example. In other embodiments, digital processing system 1030 may generate other standard or non-standard digital image formats. Digital processing system 1030 may transmit diagnostic image files (e.g., the aforementioned DICOM formatted files) to treatment planning system 2000 over a data link 1500, which may be, for example, a direct link, a local area network ("LAN") link or a wide area network ("WAN") link such as the Internet. In addition, the information transferred between systems may either be pulled or pushed across the communication medium connecting the systems, such as in a remote diagnosis or treatment planning configuration. In remote diagnosis or treatment planning, a user may utilize embodiments of the present invention to diagnose or treatment plan despite the existence of a physical separation between the system user and the patient.

Treatment planning system 2000 includes a processing device 2010 to receive and process image data. Processing device 2010 may represent one or more general-purpose processors (e.g., a microprocessor), special purpose processor such as a DSP or other type of device such as a controller or FPGA. Processing device 2010 may be configured to execute instructions for performing treatment planning operations discussed herein.

Treatment planning system 2000 may also include system memory 2020 that may include a random access memory ("RAM"), or other dynamic storage devices, coupled to processing device 2010 by bus 2055, for storing information and instructions to be executed by processing device 2010. System memory 2020 also may be used for storing temporary variables or other intermediate information during execution of instructions by processing device 2010. System memory 2020 may also include a read only memory ("ROM") and/or other static storage device coupled to bus 2055 for storing static information and instructions for processing device 2010.

Treatment planning system 2000 may also include storage device 2030, representing one or more storage devices (e.g., a magnetic disk drive or optical disk drive) coupled to bus 2055 for storing information and instructions. Storage device 2030 may be used for storing instructions for performing the treatment planning steps discussed herein.

Processing device 2010 may also be coupled to a display device 2040, such as a cathode ray tube ("CRT") or liquid crystal display ("LCD"), for displaying information (e.g., a 2D or 3D representation of the VOI) to the user. An input device 2050, such as a keyboard, may be coupled to processing device 2010 for communicating information and/or command selections to processing device 2010. One or more other user input devices (e.g., a mouse, a trackball or cursor direction keys) may also be used to communicate directional information, to select commands for processing device 2010 and to control cursor movements on display 2040.

It will be appreciated that treatment planning system 2000 represents only one example of a treatment planning system, which may have many different configurations and architectures, which may include more components or fewer components than treatment planning system 2000 and which may be employed with the present invention. For example, some systems often have multiple buses, such as a peripheral bus, a dedicated cache bus, etc. The treatment planning system 2000 may also include MIRIT (Medical Image Review and Import Tool) to support DICOM import (so images can be fused and targets delineated on different systems and then imported into the treatment planning system for planning and dose calculations), expanded image fusion capabilities that allow the user to treatment plan and view dose distributions on any one of various imaging modalities (e.g., MRI, CT, PET, etc.). Treatment planning systems are known in the art; accordingly, a more detailed discussion is not provided.

Treatment planning system 2000 may share its database (e.g., data stored in storage device 2030) with a treatment delivery system, such as radiation treatment delivery system 100, so that it may not be necessary to export from the treatment planning system prior to treatment delivery. Treatment planning system 2000 may be linked to radiation treatment delivery system 100 via a data link 2500, which may be a direct link, a LAN link or a WAN link as discussed above with respect to data link 1500. It should be noted that when data links 1500 and 2500 are implemented as LAN or WAN connections, any of diagnostic imaging system 1000, treatment planning system 2000 and/or radiation treatment delivery system 100 may be in decentralized locations such that the systems may be physically remote from each other. Alternatively, any of diagnostic imaging system 1000, treatment planning system 2000 and/or radiation treatment delivery system 100 may be integrated with each other in one or more systems.

Radiation treatment delivery system 100 includes a therapeutic and/or surgical radiation source 105 to administer a prescribed radiation dose to a target volume in conformance with a treatment plan. Radiation treatment delivery system 100 may also include an imaging system 3020 (including imaging sources 120 and detectors 115) to capture inter-treatment images of a patient volume (including the target volume) for registration or correlation with the diagnostic images described above in order to position the patient with respect to the radiation source. Radiation treatment delivery system 100 may also include a digital processing system 3030 to control radiation source 105, imaging system 3020, and a patient support device such as a treatment couch 110. Digital processing system 3030 may include one or more general-purpose processors (e.g., a microprocessor), special purpose processor such as a DSP or other type of device such as a controller or FPGA. Digital processing system 3030 may also include other components (not shown) such as memory, storage devices, network adapters and the like. Digital processing system 3030 may be coupled to radiation treatment source 105, imaging system 3020 and treatment couch 110 by a bus 3045 or other type of control and communication interface.

Figure 11:
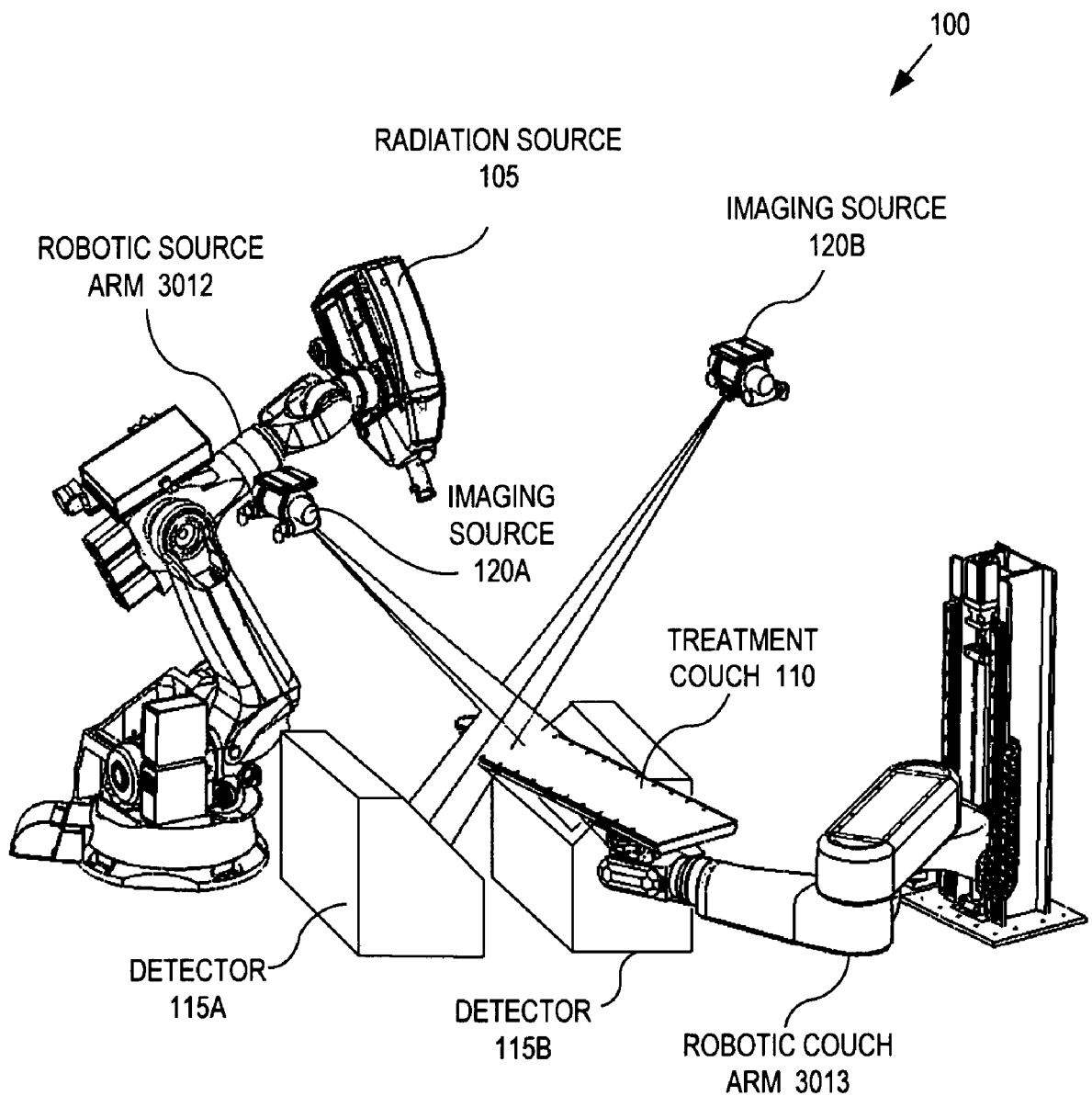
FIG. 11 is a perspective view of a radiation treatment delivery system, in accordance with an embodiment of the invention.

FIG. 11 is a perspective view of a radiation delivery system 100, in accordance with an embodiment of the invention. In one embodiment, radiation treatment delivery system 100 may be an image-guided, robotic-based radiation treatment system such as the CyberKnife® system developed by Accuray, Inc. of California. In FIG. 11, radiation source 105 may be a linear accelerator ("LINAC") mounted on the end of a source positioning system 3012 (e.g., robotic arm) having multiple (e.g., 5 or more) degrees of freedom in order to position the LINAC to irradiate a pathological anatomy (target region or volume) with beams delivered from many angles in an operating volume (e.g., a sphere) around the patient. Treatment may involve beam paths with a single isocenter (point of convergence), multiple isocenters, or with a non-isocentric approach (i.e., the beams need only intersect with the pathological target volume and do not necessarily converge on a single point, or isocenter, within the target). Treatment can be delivered in either a single session (mono-fraction) or in a small number of sessions (hypo-fractionation) as determined during treatment planning. With radiation treatment delivery system 100, in one embodiment, radiation beams may be delivered according to the treatment plan without fixing the patient to a rigid, external frame to register the intra-operative position of the target volume with the position of the target volume during the pre-operative treatment planning phase.

Imaging system 3020 (see FIG. 10) may be represented by imaging sources 120A and 120B and imaging detectors (imagers) 115A and 115B in FIG. 11. In one embodiment, imaging sources 120A and 120B are X-ray sources. In one embodiment, for example, two imaging sources 120A and 120B may be nominally aligned to project imaging x-ray beams through a patient from two different angular positions (e.g., separated by 90 degrees, 45 degrees, etc.) and aimed through the patient on treatment couch 110 toward respective detectors 115A and 115B. In another embodiment, a single large imager can be used that would be illuminated by each x-ray imaging source. Alternatively, other numbers and configurations of imaging sources and detectors may be used.

Digital processing system 3030 may implement algorithms to register images obtained from imaging system 3020 with pre-operative treatment planning images in order to align the patient on the treatment couch 110 within radiation treatment delivery system 100, and to precisely position radiation source 105 with respect to the target volume.

In the illustrated embodiment, treatment couch 110 is coupled to a couch positioning system 3013 (e.g., robotic couch arm) having multiple (e.g., 5 or more) degrees of freedom. Couch positioning system 3013 may have five rotational degrees of freedom and one substantially vertical, linear degree of freedom. Alternatively, couch positioning system 3013 may have six rotational degrees of freedom and one substantially vertical, linear degree of freedom or at least four rotational degrees of freedom. Couch positioning system 3013 may be vertically mounted to a column or wall, or horizontally mounted to pedestal, floor, or ceiling. Alternatively, treatment couch 110 may be a component of another mechanical mechanism, such as the Axum™ treatment couch developed by Accuray, Inc. of California, or be another type of conventional treatment table known to those of ordinary skill in the art.

Alternatively, radiation treatment delivery system 100 may be another type of treatment delivery system, for example, a gantry based (isocentric) intensity modulated radiotherapy ("IMRT") system or 3D conformal radiation treatments. In a gantry based system, a therapeutic radiation source (e.g., a LINAC) is mounted on the gantry in such a way that it rotates in a plane corresponding to an axial slice of the patient. Radiation is then delivered from several positions on the circular plane of rotation. In IMRT, the shape of the radiation beam is defined by a multi-leaf collimator that allows portions of the beam to be blocked, so that the remaining beam incident on the patient has a pre-defined shape. The resulting system generates arbitrarily shaped radiation beams that intersect each other at the isocenter to deliver a dose distribution to the target. In IMRT planning, the optimization algorithm selects subsets of the main beam and determines the amount of time that the patient should be exposed to each subset, so that the prescribed dose constraints are best met.

It should be noted that the methods and apparatus described herein are not limited to use only with medical diagnostic imaging and treatment. In alternative embodiments, the methods and apparatus herein may be used in applications outside of the medical technology field, such as industrial imaging and non-destructive testing of materials (e.g., motor blocks in the automotive industry, airframes in the aviation industry, welds in the construction industry and drill cores in the petroleum industry) and seismic surveying. In such applications, for example, "treatment" may refer generally to the application of radiation beam(s).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. An apparatus for performing quality assurance on a radiation treatment delivery system, the apparatus comprising:
    a housing being penetrable by a radiation beam of a radiation source of the radiation treatment delivery system and at least translucent to an image guidance system of the radiation treatment delivery system;
    a target region disposed within the housing that contrasts with the housing when imaged by the image guidance system; and
    alignment protrusions disposed on the housing for aligning a film insert relative to the target region.

2. The apparatus of claim 1, wherein the housing comprises first, second, third, and forth sections, the apparatus further comprising:
    a first connector coupling the first and second sections and constraining the first and second sections to slide relative to each other along a first axis; and
    a second connector coupling the first and third sections and constraining the first and third sections to slide relative to each other along a second axis.

3. The apparatus of claim 2, further comprising a locking mechanism mounted to at least one of the first, second, or third sections and configured to hold onto the fourth section when the first, second, and third sections are slid together and the locking mechanism is engaged.

4. The apparatus of claim 2, further comprising:
    a first latch pivotally mounted to the first section and configured to hold the first and second sections together and to latch onto the fourth section when pivoted closed; and
    a second latch pivotally mounted to the first section and configured to hold the first and third sections together and to latch onto the fourth section when pivoted closed.

5. The apparatus of claim 4, further comprising a flexible spline protruding from the first latch to urge the second section towards the first section when the first latch is pivoted closed.

6. The apparatus of claim 4, further comprising grooves disposed in the second and third sections that catch onto the first and second latches when the first and second latches are pivoted open, the grooves to prevent the first, second, and third sections from decoupling when the first and second latches are pivoted open.

7. The apparatus of claim 6, wherein the fourth section is removable from the first, second, and third sections when the first and second latches are pivoted open.

8. The apparatus of claim 2, further comprising:
    first housing alignment structures disposed on the fourth section; and
    second housing alignment structures disposed on the second and third sections that mate with the first housing alignment structures to align the fourth section to the second and third sections when the first, second, third, and fourth sections are pushed together.

9. The apparatus of claim 2, wherein the alignment protrusions are disposed on a first surface that pushes against a second surface of one of the first, second, third, or fourth sections when the housing is in a closed position.

10. The apparatus of claim 9, wherein the film insert is disposed between the first and second surfaces, the film insert including cutouts positioned to lineup with the alignment protrusions to align the film insert relative to the target region.

11. The apparatus of claim 9, wherein the film insert comprises a first film insert, the apparatus further comprising a second film insert including a second slit to match up with a first slit in the first film insert when the first and second film inserts are interlinked, wherein the first, second, third, and fourth sections of the housing support the first and second film inserts in planes substantially perpendicular to each other.

12. The apparatus of claim 1, wherein the target region supports a target split in multiple sections to permit the film insert to pass through the target region.

13. The apparatus of claim 2, further comprising:
    a plurality of grooves each disposed in one of the first, second, third, and fourth sections; and
    a plurality of sliders each disposed within a corresponding one of the grooves and shaped to slide within the grooves to secure the first, second, third, and fourth sections in a closed position.

14. The apparatus of claim 13, wherein the alignment protrusions are disposed on the sliders to mate with alignment recesses when the sliders are engaged and the first, second, third, and fourth sections are in the closed position, wherein the film insert includes cutouts for the alignment protrusions to insert through when the sliders are engaged.

15. The apparatus of claim 2, further comprising a plurality of metallic fiducials suspended within the housing.

16. A method of performing a quality assurance check on a radiation treatment delivery system, comprising:
    placing a film insert into a quality assurance ("QA") marker including multiple sections that separate to accept the film insert and secure together to hold the film insert, the QA marker including an alignment protrusion disposed on an inside surface of one of the sections to mate with a cutout in the film insert to align the film insert relative to a target region within the QA marker;
    positioning the QA marker at a preset position under guidance of an imaging guidance system of the radiation treatment delivery system;
    delivering a treatment plan of radiation to the QA marker; and
    analyzing a delivered dose image developed on the film insert to validate calibration of the radiation treatment delivery system.

17. The method of claim 16, wherein the QA marker comprise a phantom insert, the method further comprising inserting the phantom insert into an anthropomorphic phantom, wherein positioning the QA marker comprises positioning the anthropomorphic phantom, and wherein delivering the treatment plan of radiation to the QA marker comprises delivering the treatment plan of radiation to the phantom insert through the anthropomorphic phantom.

18. The method of claim 16, wherein placing the film insert into the QA marker comprises:
   inserting the film insert in between the multiple sections of the QA marker;
   sliding the multiple sections together; and
   engaging a latch to secure the sections in a closed position.

19. The method of claim 18, wherein inserting the film insert in between the multiple sections of the QA marker comprises aligning cutouts in the film insert with alignment protrusions disposed on an inside surface of one of the multiple sections.

20. The method of claim 18, wherein the multiple sections comprise four sections and wherein placing the film insert into the QA marker further comprises:
   sliding second and third sections towards a first section along sliding connectors;
   replacing a fourth section; and
   securing the fourth section to the first, second, and third sections when the latch is engaged.

21. The method of claim 20, wherein replacing the fourth section comprises aligning the fourth section to the second and third sections by mating housing alignment structures disposed on inside surfaces of the second, third, and fourth sections.

22. The method of claim 20, further comprising urging the second section towards the first section with a flexible spline disposed on the latch when the latch is engaged.

23. An apparatus for performing quality assurance on a radiation treatment delivery system, the apparatus comprising:
   housing means for rigidly holding a radiographic film insert;
   alignment means for aligning the radiographic film insert relative to a target region disposed within the housing means; and
   securing means for securing the housing means in a closed position, wherein the housing means comprises four separable sections, the apparatus further comprising:
   means for coupling a first section of the housing means to a second section of the housing means and for constraining the first and second sections to slide relative to each other along a first axis; and
   means for coupling the first section to a third section of the housing means and for constraining the first and third sections to slide relative to each other along a second axis.

24. The apparatus of claim 23, wherein the securing means comprises a latching means for latching onto a fourth section of the housing means.

25. The apparatus of claim 24, further comprising means for urging the second and third sections towards the first section.

26. The apparatus of claim 24, further comprising means for aligning the fourth section to the second and third sections.

27. The apparatus of claim 26, wherein the second alignment means are disposed on the slider means.

28. The apparatus of claim 23, means for stopping the first, second, and third sections from decoupling when the housing means is in an open position.

29. The apparatus of claim 23, wherein the securing means comprises slider means for securing the housing means in the closed position by sliding into an engaged position.

* * * * *